United States Patent [19]
Williams, Jr.

[11] Patent Number: 5,441,040
[45] Date of Patent: Aug. 15, 1995

[54] RDS SPECULUM

[76] Inventor: Barney K. Williams, Jr., Kerrville, Tex.

[21] Appl. No.: 190,315

[22] Filed: Feb. 2, 1994

[51] Int. Cl.⁶ ............................................. A61B 19/00
[52] U.S. Cl. .................................... 600/236; 606/107; 606/191; 600/232
[58] Field of Search ......................... 128/20, 3, 17, 18; 606/107, 191, 198, 1, 162; D24/135, 150, 172; D28/36

[56] References Cited

U.S. PATENT DOCUMENTS

| | | | |
|---|---|---|---|
| 4,037,589 | 7/1977 | McReynolds | 128/20 |
| 5,171,254 | 12/1992 | Sher | 128/20 X |
| 5,290,292 | 3/1994 | Householder | 128/20 X |

FOREIGN PATENT DOCUMENTS

| | | | |
|---|---|---|---|
| 712704 | 10/1931 | France | 128/17 |
| 71126 | 10/1946 | Norway | 606/191 |
| 116312 | 6/1918 | United Kingdom | 128/20 |

OTHER PUBLICATIONS

John Reynders & Co. Catalog, p. 166 (New York, 1985).

*Primary Examiner*—Richard J. Apley
*Assistant Examiner*—Beverly M. Flanagan
*Attorney, Agent, or Firm*—Gunn, Lee & Miller

[57] ABSTRACT

An improved speculum for increased exposure of the superior surgical limbus and stabilization of the eye during eye surgery.

16 Claims, 4 Drawing Sheets

RDS SPECULUM

BACKGROUND OF THE INVENTION

1. Field of The Invention

Applicant's invention relates to an improved speculum for use in cataract surgery, secondary intraocular lens replacement, intraocular lens removal or repositioning, and glaucoma surgery and other surgeries that require access to the eye. Specifically, applicant's invention provides increased exposure, via eyeball depression and eyelid retraction, of the superior surgical limbus that has previously only been obtained by utilizing a fixation suture that pierced the superior rectus tendon. Applicant's invention also provides stabilization of the eyeball not provided by prior art speculums.

2. Background of The Invention

A variety of speculums are currently on the market. See FIG. 1 and FIG. 2 (Prior Art). Yet, none of the prior art speculums allow sufficient access to the superior surgical limbus without utilizing a suture that penetrates the superior rectus tendon. Although not proven, the consensus in the medical community is that the suture causes a postoperative drooping of the upper eyelid. In some instances, the post operative droop does not disappear and may only be corrected by additional surgeries. Thus, the patient may be left with a permanent droopy eye. Consequently, a need exists for a speculum that affords the necessary access, yet does not require suturing.

In addition to not affording the necessary access without suturing, prior art speculums do not afford the necessary stability and rotation of the eyeball for delicate surgical maneuvers. For example, when prior art speculums are utilized the eyeball may shift at an inopportune time and cause damage to the eye. Accordingly, a need exists for a speculum that affords increased stability and rotation of the eyeball.

Finally, the prior art speculums do not maintain the upper and lower eyelids in an extended retracted position. The manner in which the superior arm and the inferior arm of the prior art speculums are connected allow the weight of the eyelids to push the retractor arms of the speculum together. Consequently, the surgical area is further decreased because the retractor arms of the speculum are incapable of maintaining the eyelids in an extended retracted position. Accordingly, a need exists for a speculum that maintains the upper and lower eyelid in a more distant relationship than is currently available.

SUMMARY OF THE INVENTION

Applicant's invention finds great utility in conjunction with surgical maneuvers that require exposure of the superior surgical limbus and/or stabilization of the eyeball. In accordance with this invention, an improved speculum has been developed which incorporates a superior arm with an offset retractor and an inferior arm with a retractor attached to an eye contacting segment. The offset retractor of the superior arm increases exposure to the superior surgical limbus. The retractor of inferior arm in conjunction with the eye contacting segment depress the eyeball downwards to stabilize vertical movement of the eyeball and simultaneously stabilize lateral movement of the eyeball. Applicant's invention may also include an improved base which has V-shaped arm components connected by a spacing arm. This structure assures the superior and inferior arms are maintained in a distant relationship during surgery.

Therefore, it is an object of this invention to afford the surgeon the necessary access to the superior surgical limbus without suturing.

It is another object of this invention to provide the surgeon with decreased eye movement during surgery.

It is a further object of this invention to assure the upper eyelid and lower eyelid remain separated during surgery.

Other objects of this invention and advantages of this invention will be readily apparent to those skilled in the art from the following detailed description, taken in conjunction with the annexed sheets of drawings, which illustrate the preferred embodiment of the invention.

DETAILED DESCRIPTION OF THE PREFERRED EMBODIMENT

The following detailed description is provided to aid those skilled in the art to practice the present invention. Even so, the following discussion should not be deemed to unduly limit the present invention, since modifications may easily be made in the procedures herein taught by one of ordinary skill in the art, without departing from the spirit or scope of the present invention. In this regard, the present invention is only to be limited by the scope of the claims appended hereto and equivalents thereof.

Figure 3:
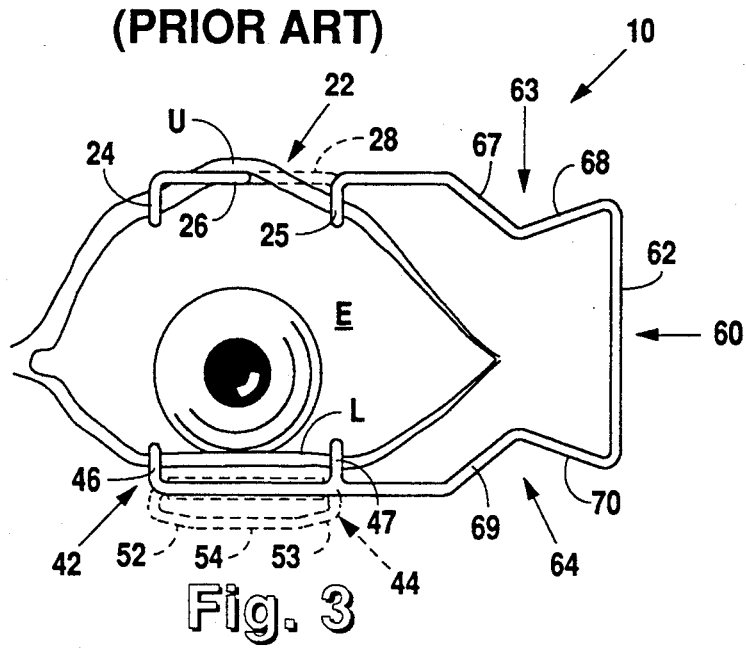
FIG. 3 is a frontal view of applicant's speculum in use.
Figure 4:
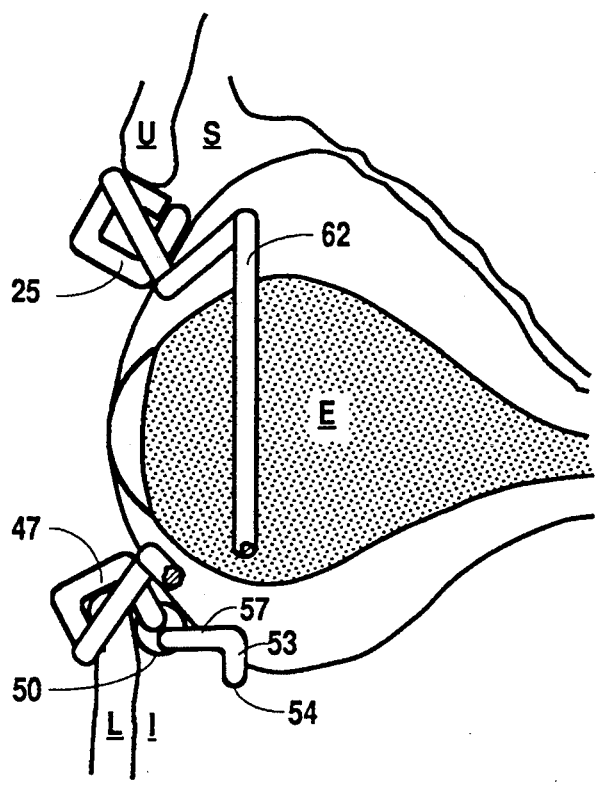
FIG. 4 is a cutaway side view of applicant's speculum in use.
Figure 5:
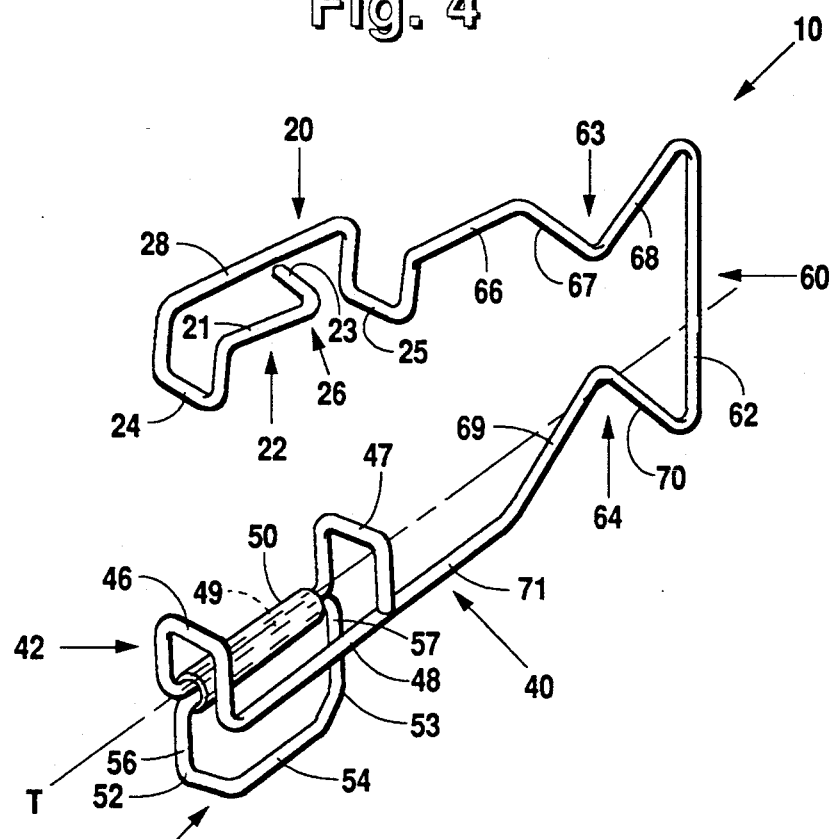
FIG. 5 is a perspective view of applicant's speculum for use with the left eye.

FIG. 5 illustrates the preferred embodiment of speculum (10) apart from eyeball (E) as illustrated in FIGS. 3 & 4. Referring to FIG. 5, speculum (10) is comprised of superior arm (20), inferior arm (40), and base (60). Superior arm (20) is comprised of superior retractor (22) for maintaining upper eyelid (U) (see FIG. 3) in proper surgical position. Inferior arm (40) is comprised of inferior retractor (42) and eye contacting segment (44). Inferior retractor (42) in conjunction with eye contacting segment (44) maintains lower eyelid (L) (see FIG. 3) in proper position for surgery and stabilizes and minimizes eyeball's (E) (see FIG. 3) horizontal and vertical movement.

Superior retractor (22) is comprised of first holding well (24), second holding well (25), offset bar (26) and first holding well connecting bar (28) which attaches first holding well (24) to second holding well (25). First holding well connecting bar (28) slopes slightly downward from first holding well (24) to second holding well (25). This downward sloping effectuates a horizontal adjustment when speculum (10) is in use. Referring to FIG. 3, when in use, first holding well (24) is forced further downward than second holding well (25) to a point that holding well connecting bar (28) appears not to slope.

As shown in FIG. 3, offset bar (26) of superior retractor (22) allows additional access to the superior surgical limbus. Prior art speculum (100) (FIG. 1) does not include this feature and consequently the mid-portion of upper eyelid (U) droops down into the surgical area. (See FIG. 2.) In using prior art speculum (100) a suture (not shown) is utilized to tack the mid section of upper eyelid (U) upwards to obtain the necessary access. As shown in FIG. 3, offset bar (26) of superior retractor (22) of speculum (10) allows the necessary access by maintaining the midsection of upper eyelid (U) in a higher position without a suture. This is an important feature because suturing is believed to cause droopy upper eyelids.

As shown in FIG. 5, offset bar (26) is generally L-shaped with first leg component (21) and second leg component (23). First leg component (21) slopes generally downward and reaches its lowest point where first leg component (21) and second leg component (23) meet. Second leg component (23) slopes generally upward from its meeting point with first leg component (21) to a final height generally equal to the height of holding well connecting bar (28). At its lowest point, first leg component (21) is approximately 2 mm below holding well connecting bar (28).

Although FIGS. 3 and 5 illustrate the preferred embodiment of offset bar (26), offset bar (26) may also be attached to second holding well (25) instead of first holding well (24). In addition, offset bar could be replaced by other structures which would effect increased access. For example, an arm component could be attached to both holding well (24) and holding well (25) in such a manner that it would peak at its mid-point to cause upper eyelid (U) to rise. In another version, offset bar (26) may only include second leg component (23) rigidly attached to the midpoint of first holding well connecting bar (28). Other means of configuring superior retractor (22) will be apparent to those skilled in the art.

Referring again to FIG. 5, inferior retractor (42) is comprised of third holding well (46), fourth holding well (47), second holding well connecting bar (48) and third holding well connecting bar (49). Eye contacting segment (44) is maintained adjacent to third holding well connecting bar (49) by smooth sleeve (50) so that eye contacting segment (44) may both pivot about and slide longitudinally along axis (T), with axis (T) being parallel to third holding well connecting arm (49). This movement allows eye contacting segment (44) to vertically and laterally accommodate the patient's individual inferior fornix. Those skilled in the art will recognize other means of maintaining eye contacting segment (44) adjacent to inferior retractor (42), but which also allows eye contacting segment to pivot and slide along axis (T). For example, such means could include hinges, clips, screws, and other smooth connecting means which would not puncture, scratch or damage eyeball (E) when speculum (10) is in use.

In the preferred embodiment, eye contacting segment (44) is comprised of first contacting corner (52), second contacting corner (53), recessed mid section (54), first extension arm component (56) and second extension arm component (57). In modified versions, eye contacting segment (44) may not include a recessed mid-section (54) or may be further recessed dependent on the curvature of the patient's eye.

Referring to FIG. 4, when speculum (10) is in use, first contacting corner (52) (not shown) and second contacting corner (53) contact eyeball (E). At least a portion of recessed mid section (54) of eye contacting segment (44) will also contact eyeball (E). The amount of contact is dependant on the curvature of the patient's eyeball. Eye contacting segment (44) in conjunction with inferior retractor (42) depresses and rotates the eye downward to expose the superior surgical limbus and stabilize vertical and lateral movement of the eye. Prior art speculum (100) (FIGS. 1 and 2) does not have an eye contacting segment (44). Consequently, surgeries using prior art speculum (100) have a higher tendency for eyeball movement which makes the surgeries more difficult.

Referring to FIG. 5, base (60) is comprised of spacer arm (62), first pressure arm (63) and second pressure arm (64). First pressure arm (63) is comprised of horizontal arm component (66), first sloping arm component (67) and second sloping arm component (68). Horizontal arm component (66) is rigidly connected to second holding well (25). Second pressure arm (64) is comprised of horizontal arm component (71), first sloping arm component (69) and second sloping arm component (70). Horizontal arm component (71) may be either an extension of second holding well connecting bar (48) of inferior retractor (42) or it may be a separate piece rigidly connected to second holding well connecting bar (48).

Figure 6:
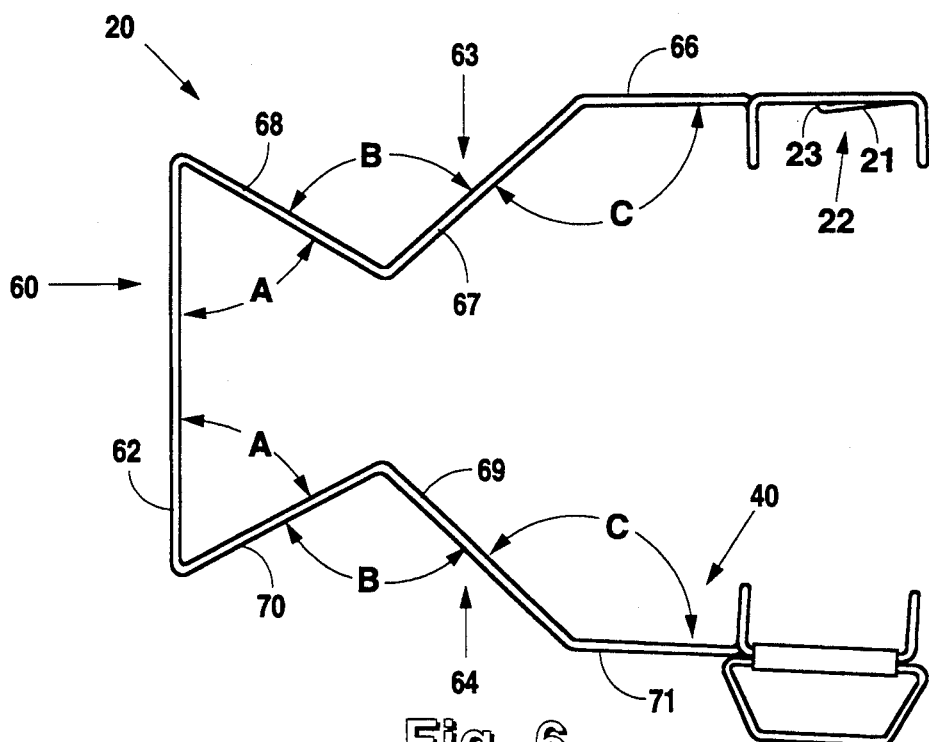
FIG. 6 is a side view of applicant's speculum illustrating various angle measurements.

Referring to FIG. 6 in the preferred embodiment, the top edge of spacer arm (62) is connected to the upper edge of second sloping arm component (68) of pressure arm (63) at approximately a 60 degree angle (A). The lower edge of second sloping arm component (68) of first pressure arm (63) is rigidly connected to the lower edge of first sloping arm component (67) of first pressure arm (63) at approximately a 110 degree angle (B). The upper edge of first sloping arm component (67) of first pressure arm (63) is rigidly connected to horizontal arm component (66) at approximately a 140 degree angle (C). The bottom edge of spacer arm (62) is rigidly connected to the lower edge of second sloping arm component (70) at approximately a 60 degree angle (A). The upper edge of first sloping arm component (69) of pressure arm (64) is rigidly connected to the upper edge of second sloping arm component (70) of pressure arm (64) at approximately a 110 degree angle (B). The lower edge of first sloping arm component (69) of second pressure arm (64) is rigidly connected to horizontal arm component (71) of second pressure arm (64) at approximately a 140 degree angle (C). In other embodiments, Angles A, B and C may be ±5 degrees than those angles previously listed.

Figure 7:
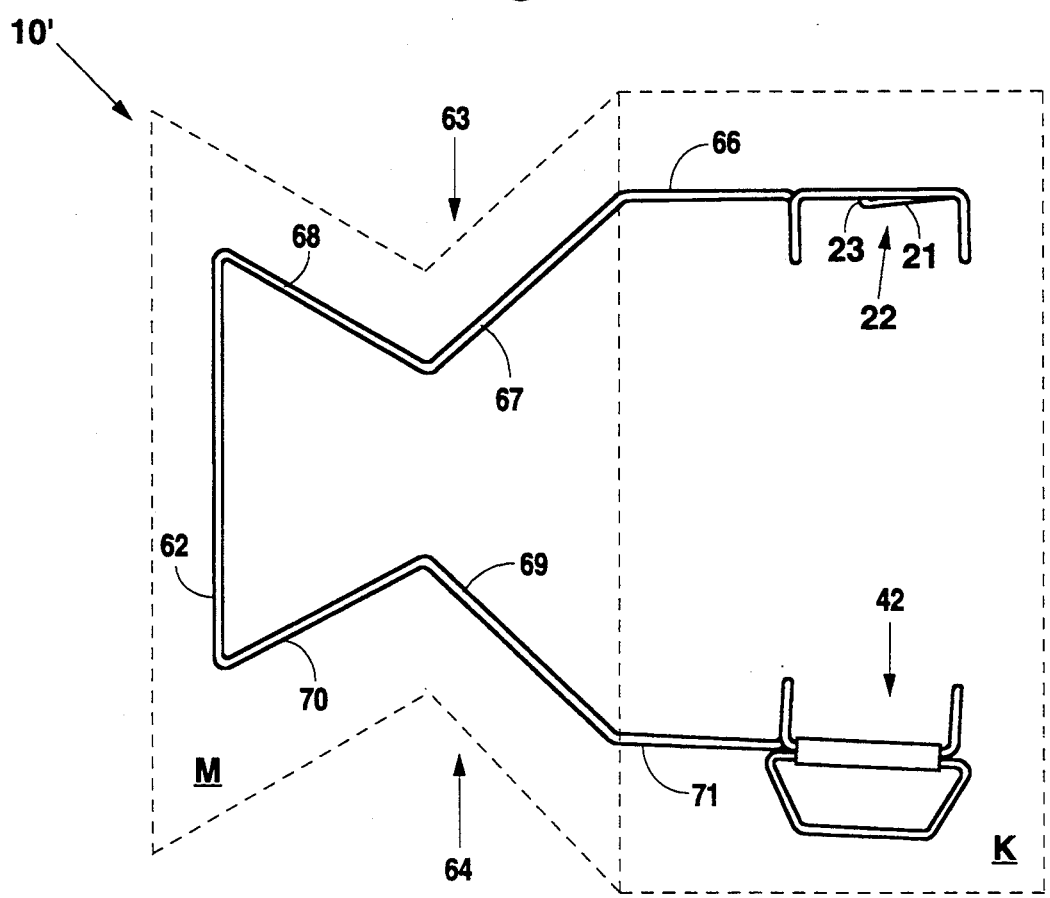
FIG. 7 is a side view of applicant's speculum illustrating the two planes which a modified version of applicant's speculum encompasses.

As shown in FIG. 6, base (60), superior arm (20), and inferior arm (40) lie in one plane. In a modified version, speculum (10') does not lie in one plane. As shown in FIG. 7, superior retractor (22), horizontal arm component (66) of first pressure arm (63), inferior retractor (42), and horizontal arm component (71) of second pressure arm (64) lie in plane (K). First sloping arm component (67) of first pressure arm (63), first sloping arm component (69) of second pressure arm (64), second sloping component arm (68) of first pressure arm (63), second sloping arm component (70) of second pressure arm (64), and spacer arm (62) lie in plane (M). Planes (K) and (M) are graphically illustrated in FIG. 7.

This curvature allows speculum (10') to conform to the slope of a person's face, thus allowing unhindered access to the surgical area because no portion of speculum (10') will be in the way of tools and other surgical items. In normal use, plane (M) is at a 40 degree ±5 degrees turn down angle to plane (K). Of course, depending on the type of materials speculum (10') is composed of, planes (M) and (K) may be further adjusted to align with a patient's particular facial structure and thus the turn down angle may be larger or smaller dependent on the patient's facial structure. In either embodiment, spacer bar (62) is generally perpendicular to axis (T) and horizontal arm components (66 and 71) are generally parallel to axis (T). (See FIG. 5.)

Figure 1:
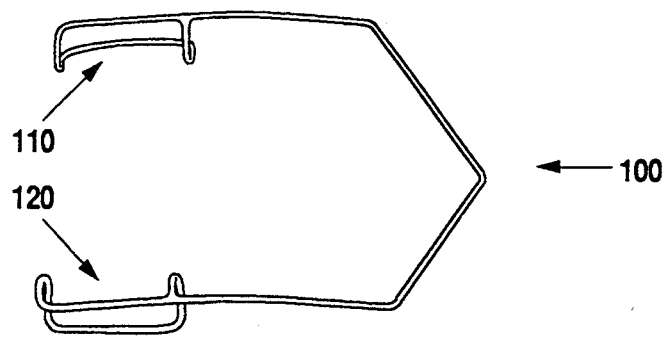
FIG. 1 is a perspective view of prior art.
Figure 2:
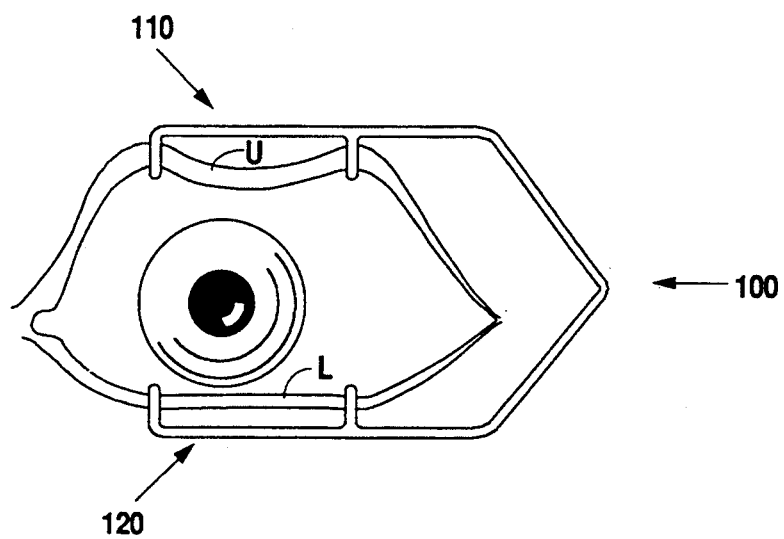
FIG. 2 is a frontal view of a prior art speculum in use.

Referring to FIG. 5, the particular shape of base (60) of speculum (10) also assists in maintaining superior retractor (22) and inferior retractor (42) a sufficient distance apart to assure access to the surgical area. In the prior art as illustrated in FIGS. 1 and 2, superior retractor (110) and inferior retractor (120) remain separated only on the strength of the particular material used because no other portion of speculum (100) assists superior retractor (110) and inferior retractor (120) in maintaining upper eyelid (U) and lower eyelid (L) apart. As illustrated in FIG. 3, the configuration of spacer arm (62), first pressure arm (63), and second pressure arm (64) assist in maintaining superior retractor (22) and inferior retractor (42) apart.

Again, referring to FIG. 5, in the preferred embodiment, superior retractor (22) and inferior retractor (42) are approximately 12 mm ±2 mm in length, 5 mm ±2 mm deep and 4 mm ±2 mm wide. First leg component (21) of offset bar (26) of superior retractor (22) is approximately 6 mm ±2 mm long. Second leg component (23) of offset bar (26) of superior retractor (22) is approximately 4 mm ±2 mm long. Horizontal arm component (66) and horizontal arm component (71) are approximately 12 mm ±2 mm long. First sloping arm component (67) and second sloping arm component (68) of first pressure arm (63) and first sloping arm component (69) and second sloping arm component (70) of second pressure arm (64) are approximately 15 mm ±2 mm long. Spacer arm (62) is approximately 30 mm ±2 mm long. Recessed mid-section (54) of eye contacting segment (44) is recessed approximately 7 mm ±2 mm and is approximately 10 mm ±2 mm in length. First extension arm component (56) and second extension arm component (57) are approximately 16 mm ±2 mm apart. Of course, these measurements are only the preferred adult version and should not be used to limit Applicant's invention because the measurements may change dependent on the patient's size. For example, a young child will require a smaller version.

The manner in which speculum (10) is constructed will be dependant on the type of materials utilized. If speculum (10) is composed of a bendable material, then the necessary curves and angles may be obtained without connecting separate pieces of material. On the other hand, if a bendable material is not utilized, then each arm, holding well and so forth may be attached as a separate piece or attached in sections. If a moldable plastic is used, speculum (10) may be prepared as one unit. The preferred material is non-corrosive wire, flexible enough to compress superior and inferior arms together for insertion between the eyelids, yet cause superior and inferior arms to return to their original separation distance after use. The preferred composition material being 0.9 mm ±0.1 mm diameter stainless steel wire.

Figure 8:
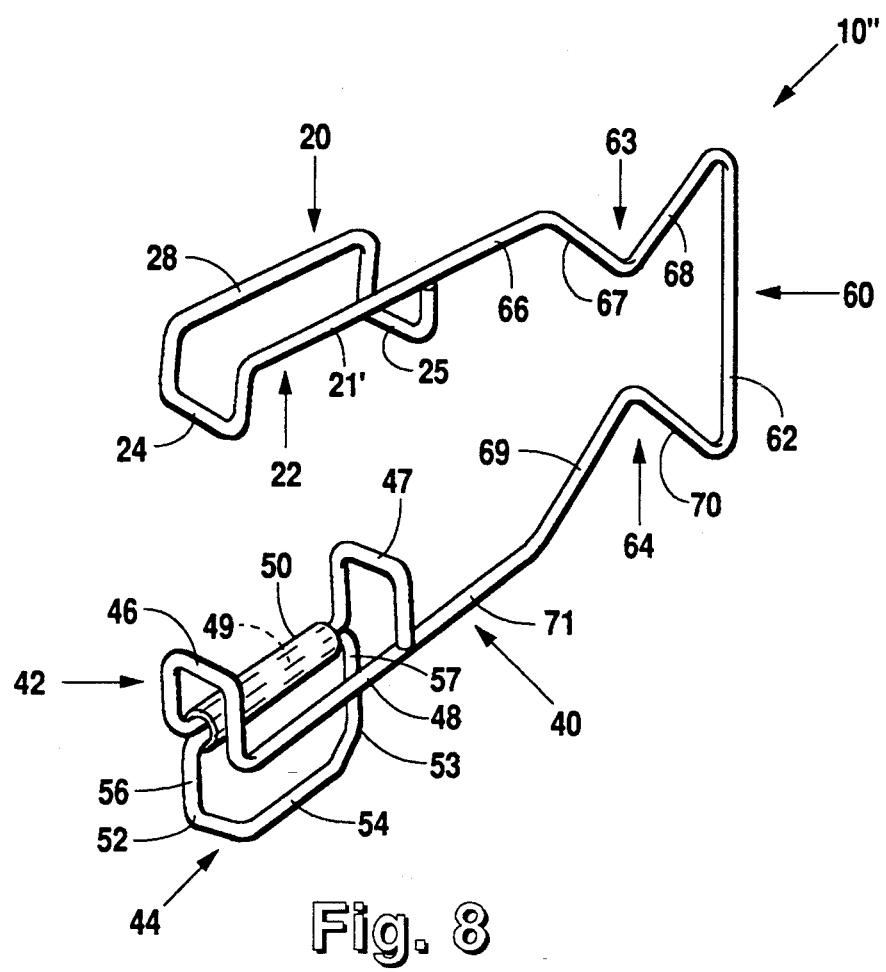
FIG. 8 is a perspective view of Applicant's speculum without the middle extension.

FIG. 8 illustrates a second modified version of speculum (10'). The construction is the same as illustrated in FIG. 5 for speculum (10) with the only difference being that offset bar (26) has been replaced by a modified first leg component (21'). The modified first leg component (21') extends from first holding well (24) to second holding well (25) and is also designated as a parallel connecting bar. Modified version (10") is used in the instances wherein the surgeon also utilizes a plastic drape. Some surgeons use a plastic drape to cover the surgical area in hopes of minimizing infection. The plastic drape initially covers the eye and then is slit to expose the eye. The underneath side of the plastic drape is adhesive and envelopes the lid margin of upper eyelid (U) and lower eyelid (L). The enveloped lid margins are thicker and more rigid, and are not maintained in the necessary position by the speculum (10) which includes offset bar (26). To correct this problem, offset bar (26) has been removed from modified version of speculum (10") and replaced with first leg (21'). Base (60) remains the same.

Referring to FIGS. 3 and 4, to use speculum (10), eye contacting segment (44) and third holding well connecting bar (49) are inserted into the inferior fornix (I) of the patient's eye. First contacting corner (52) and second contacting corner (53) of eye contacting segment (44) contact eyeball (E). A portion of recessed mid-section (54) of eye contacting segment (44) also contacts eyeball (E). Eye contacting segment (44) is pivotally and longitudinally adjusted to effect the greatest contact between eye contacting segment (44) and eyeball (E). This contact between eyeball (E) and first contacting corner (52), second contacting corner (53) and a portion of recessed mid-section (54) stabilizes vertical movement of eyeball (E) and causes increased exposure of the superior surgical limbus by depressing and rotating the eyeball downward. Lower lid (L) is retained in third holding well (46) and forth holding well (47) of inferior retractor (42). First holding well connecting bar (28) of superior retractor (22) is then inserted in the superior fornix (S) of the patient's eye. The upper lid (U) of the patient is supported by first holding well (24) and second holding well (25). Offset bar (26) further supports upper eyelid (U). Superior retractor (22) and inferior retractor (42) may be pushed closer together by putting pressure on first sloping arm component (67) of first pressure arm (63) and first sloping arm component (69) of second pressure arm (64). If further access to eye is required, superior retractor (22) and inferior retractor (42) may be pushed further apart by forcing first sloping arm component (67) of first pressure arm (63) and first sloping arm component (69) of second pressure arm (64) further apart. After the surgery is complete, the speculum (10) is removed in the reverse order discussed above and the eyelids are allowed to close.

I claim:

1. An improved speculum for use in eye surgery on a patient's eye having an eyeball, a superior surgical limbus, an upper eyelid and a lower eyelid, wherein said speculum comprises:

a superior arm with a first end and a second end;
an inferior arm with a first end and a second end;
said second end of said superior arm connected to said second end of said inferior arm by a connecting means;

said first end of said superior arm comprising a retractor means for maintaining the upper eyelid of said patient's eye in an open position, wherein said retractor means of said superior arm further comprises:
  a first U-shaped holding well connected to a second U-shaped shaped holding well by a first holding well connecting bar with each of said first and said second holding wells having a proximate side member and a distal side member in relationship to said patient's eye when said speculum is in use; and
  an offset bar allowing additional access to the superior surgical limbus of the patient's eye, wherein said offset bar is connected to one of said first or said second holding wells; and
said first end of said inferior arm comprising a retractor means for maintaining said lower eyelid of patient's eye in an open position.

2. The speculum of claim 1, wherein said offset bar comprises a first leg component and a second leg component, said first leg component connected to said second leg component at approximately a 90 degree angle, said first leg component connected to said distal side member of said first U-shaped holding well such that said first leg component is generally parallel to said first holding well connecting bar and said second leg component is generally directed towards said first holding well connecting bar.

3. The speculum of claim 1, wherein said connecting means is comprised of a spacer arm positioned between two parallel V-shaped pressure arms.

4. An improved speculum for use in eye surgery on a patient's eye having an eyeball, a superior surgical limbus, an upper eyelid and a lower eyelid, wherein said speculum comprises:
  a superior arm with a first end and a second end;
  an inferior arm with a first end and a second end;
  said second end of said superior arm connected to said second end of said inferior arm by a connecting means;
  said first end of said superior arm comprising a retractor means for maintaining the upper eyelid of said patient's eye in an open position;
  said first end of said inferior arm comprising a retractor means for maintaining said lower eyelid of said patient's eye in an open position, wherein said retractor means of said inferior arm further comprises a third U-shaped holding well connected to a fourth U-shaped holding well by a second holding well connecting bar; and
  an eye contacting means maintained adjacent to said second holding well connecting bar of said retractor means of said inferior arm by a securing means which allows said eye contacting means to pivot about and slide longitudinally along an axis parallel to said second holding well connecting bar.

5. The speculum of claim 4, wherein said eye contacting means simultaneously depresses and rotates the eyeball of said patient's eye downward giving exposure to the superior surgical limbus of said patient's eye, and stabilizing vertical movement of the eyeball of said patient's eye.

6. The speculum of claim 4, wherein said retractor means of said superior arm further comprises:
  a first U-shaped holding well connected to a second U-shaped holding well by a first holding well connecting bar with each of said first and said second holding wells having a proximate side member and a distal side member in relationship to said patient's eye when said speculum is in use; and
  a parallel connecting bar extending from said distal side member of said first U-shaped holding well to said distal side member of said second U-shaped holding well.

7. The speculum of claim 4, wherein said connecting means is comprised of a spacer arm positioned between two parallel V-shaped pressure arms.

8. An improved speculum for use in eye surgery on a patient's eye having an eyeball, a superior surgical limbus, an upper eyelid and a lower eyelid, wherein said speculum comprises:
  a superior arm with a first end and a second end;
  an inferior arm with a first end and a second end;
  said second end of said superior arm connected to said second end of said inferior arm by a connecting means;
  said first end of said superior arm comprising a retractor means for maintaining the upper eyelid of said patient's eye in an open position, wherein said retractor means of said superior arm further comprises:
    a first U-shaped holding well connected to a second U-shaped holding well by a first holding well connecting bar with each of said first and said second holding wells having a proximate side member and a distal side member in relationship to said patient's eye when said speculum is in use; and
    an offset bar allowing additional access to the superior surgical limbus of the patient's eye, wherein said offset bar is connected to one of said first or said second holding wells;
  said first end of said inferior arm comprising a retractor means for maintaining said lower eyelid of said patient's eye in an open position, wherein said retractor means of said inferior arm further comprises a third U-shaped holding well connected to a fourth U-shaped holding well by a second holding well connecting bar; and
  an eye contacting means maintained adjacent to said second holding well connecting bar of said retractor means of said inferior arm by a securing means which allows said eye contacting means to pivot about and slide longitudinally along an axis parallel to said second holding well connecting bar.

9. The speculum of claim 8, wherein said offset bar comprises a first leg component and a second leg component, said first leg component connected to said second leg component at approximately a 90 degree angle, said first leg component connected to said distal side member of said first U-shaped holding well such that said first leg component is generally parallel to said first holding well connecting bar and said second leg component is generally directed towards said first holding well connecting bar.

10. The speculum of claim 8, wherein said eye contacting means simultaneously depresses and rotates the eyeball of said patient's eye downward giving exposure to the superior surgical limbus of said patient's eye, and stabilizing vertical movement of the eyeball of said patient's eye.

11. The speculum of claim 8, wherein said connecting means is comprised of a spacer arm positioned between two parallel V-shaped pressure arms.

12. A method of obtaining increased access during eye surgery to the superior surgical limbus of a patient's eye without utilizing a suture, said patient's eye having an eyeball, a superior surgical limbus, an upper eyelid, a lower eyelid and an inferior fornix, comprising the steps of:

positioning proximate to the patient's eye a speculum comprising:

a superior arm with a first end and a second end;

an inferior arm with a first end and a second end;

said second end of said superior arm connected to said second end of said inferior arm by a connecting means;

said first end of said superior arm comprising a retractor means for maintaining the upper eyelid of said patient's eye in an open position, wherein said retractor means of said superior arm further comprises:

a first U-shaped holding well connected to a second U-shaped holding well by a first holding well connecting bar with each of said first and said second holding wells having a proximate side member and a distal side member in relationship to said patient's eye when said speculum is in use; and an offset bar allowing additional access to the superior surgical limbus of the patient's eye, wherein said offset bar is connected to one of said first or said second holding wells;

said first end of said inferior arm comprising a retractor means for maintaining said lower eyelid of said patient's eye in an open position, wherein said retractor means of said inferior arm further comprises a third U-shaped holding well connected to a fourth U-shaped holding well by a second holding well connecting bar; and an eye contacting means maintained adjacent to said second holding well connecting bar of said retractor means of said inferior arm by a securing means which allows said eye contacting means to pivot about and slide longitudinally along an axis parallel to said second holding well connecting bar;

inserting said eye contacting means into the inferior fornix of said patient's eye to simultaneously depress and rotate the eyeball of said patient's eye downward giving exposure to the superior surgical limbus of said patient's eye, and stabilizing vertical movement of the eyeball of said patient;

engaging the lower eyelid of said patient's eye with said retractor means of said inferior arm to maintain the lower eyelid of said patient's eye in an open position during said surgery; and engaging the upper eyelid of said patient's eye with said retractor means of said superior arm to maintain the upper eyelid of said patient's eye in an open position during said surgery.

13. The method of claim 12, further comprising:

adjusting said eye contacting means in both a vertical and horizontal direction to effect the greatest contact between said patient's eye and said eye contacting means.

14. A method of obtaining increased access during eye surgery to the superior surgical limbus of a patient's eye without utilizing a suture, said patient's eye having an eyeball, a superior surgical limbus, an upper eyelid, a lower eyelid and a inferior fornix, comprising the steps of:

positioning proximate to the patient's eye said speculum of claim 1, engaging the lower eyelid of said patient's eye with said retractor means of said inferior arm to maintain the lower eyelid of said patient's eye in an open position during said surgery; and engaging the upper eyelid of said patient's eye with said retractor means of said superior arm to maintain the upper eyelid of said patient's eye in an open position during said surgery.

15. A method of obtaining increased access during eye surgery to the superior surgical limbus of a patient's eye without utilizing a suture, said patient's eye having an eyeball, a superior surgical limbus, an upper eyelid, a lower eyelid and a inferior fornix, comprising the steps of:

positioning proximate to the patient's eye said speculum of claim 4, inserting said eye contacting means into the inferior fornix of said patient's eye to simultaneously depress and rotate the eyeball of said patient's eye downward giving exposure to the superior surgical limbus of said patient's eye, and stabilizing vertical movement of the eyeball of said patient;

engaging the lower eyelid of said patient's eye with said retractor means of said inferior arm to maintain the lower eyelid of said patient's eye in an open position during said surgery; and engaging the upper eyelid of said patient's eye with said retractor means of said superior arm to maintain the upper eyelid of said patient's eye in an open position during said surgery.

16. The method of claim 15, further comprising:

adjusting said eye contacting means in both a vertical and horizontal direction to effect the greatest contact between said patient's eye and said eye contacting means.

* * * * *